United States Patent [19]

Pesa et al.

[11] 4,398,039
[45] Aug. 9, 1983

[54] HYDROGENATION OF CARBOXYLIC ACIDS

[75] Inventors: Frederick A. Pesa, Aurora; Anne M. Graham, Northfield; Wayne R. Kliewer, North Randall, all of Ohio

[73] Assignee: The Standard Oil Company, Cleveland, Ohio

[21] Appl. No.: 264,755

[22] Filed: May 18, 1981

[51] Int. Cl.³ ............... C07C 67/00; C07C 67/08; C07C 69/24

[52] U.S. Cl. ..................... 560/265; 252/472; 252/473; 252/474; 260/409; 260/410.9 R; 568/885

[58] Field of Search .......... 560/265; 260/410.9 R, 260/409; 568/885; 252/472, 473, 474

[56] References Cited

U.S. PATENT DOCUMENTS

| | | | |
|---|---|---|---|
| 1,839,974 | 1/1932 | Lazier | 568/885 |
| 2,093,159 | 9/1937 | Schmidt . | |
| 2,110,483 | 3/1938 | Guyer . | |
| 2,275,152 | 3/1942 | Lazier | 568/885 |
| 2,322,098 | 6/1943 | Schmidt . | |
| 2,340,687 | 2/1944 | Richardson et al. | 568/885 |
| 2,607,807 | 8/1952 | Ford | 568/885 |
| 2,750,263 | 12/1956 | De Nora et al. | 568/885 |
| 2,782,243 | 2/1957 | Hess et al. | 568/885 |
| 2,863,928 | 12/1958 | Pudest | 568/885 |
| 2,965,660 | 12/1960 | Heise et al. | 560/265 |
| 3,280,199 | 10/1966 | Schmerling | 568/885 |
| 3,361,832 | 1/1968 | Pine et al. | 568/885 |
| 3,478,112 | 11/1969 | Adam et al. | 568/885 |
| 3,729,520 | 4/1972 | Rutzen et al. | 568/885 |
| 3,848,003 | 11/1974 | Mesich et al. | 568/885 |
| 3,855,319 | 12/1974 | Hobbs et al. | 568/885 |
| 4,104,478 | 8/1978 | Trivedi | 568/885 |
| 4,113,662 | 9/1978 | Wall | 568/864 |
| 4,270,015 | 5/1981 | Knifton | 560/263 |

Primary Examiner—Vivian Garner
Attorney, Agent, or Firm—Joseph G. Curatolo; Herbert D. Knudsen; Larry W. Evans

[57] ABSTRACT

A process is provided for the vapor phase hydrogenation of carboxylic acids to yield their corresponding alcohols in the presence of steam and a catalyst comprising the mixed oxides of ruthenium, at least one of cobalt, nickel, and optionally one of cadmium, zinc, copper, iron, rhodium, palladium, osmium, iridium and platinum. A process is further provided for the preparation of carboxylic acid esters from carboxylic acids in the absence of steam utilizing the above-identified catalysts.

6 Claims, No Drawings

HYDROGENATION OF CARBOXYLIC ACIDS

BACKGROUND OF THE INVENTION

This invention relates to the hydrogenation of carboxylic acids to form alcohols. More specifically the invention relates to the vapor phase catalytic hydrogenation of carboxylic acids.

Carboxylic acids may be obtained from the carboxylation of olefins. The hydrogenation of carboxylic acids and their derivatives to obtain alcohols has previously been described in the art. The product alcohols are useful as solvents, chemical intermediates, and fuel. U.S. Pat. No. 2,093,159 discloses the catalytic hydrogenation of esters of carboxylic acids over catalytic substances such as copper, nickel, silver, zinc, cadmium, lead or cobalt and activating substances such as various transition metals, alkali metals, alkaline earth metals or rare earth metals.

U.S. Pat. No. 2,110,483 discloses a process for the manufacture of higher molecular weight alcohols from aliphatic carboxylic acids and their derivatives by hydrogenation under pressures of between 50 and 400 atmospheres and in the presence of catalysts which include copper, chromium, nickel, uranium, cobalt, zinc, cadmium, molybdenum, tungsten and vanadium.

U.S. Pat. No. 2,275,152 discloses the catalytic hydrogenation of carboxylic acid anhydrides over a mixture of chromites or chromates of hydrogenating metals selected from silver, cadmium, copper, lead, mercury, tin, bismuth, iron, cobalt, nickel, magnesium, zinc and manganese.

U.S. Pat. No. 2,322,098 and its related patents disclose the catalytic hydrogenation of alicyclic carboxylic acids in the presence of catalysts similar to those set forth in U.S. Pat. No. 2,093,159.

U.S. Pat. No. 2,607,807 discloses the preparation of alcohols from carboxylic acids in the liquid phase in the presence of a catalyst containing ruthenium and optionally sodium, potassium, barium, silver, calcium, strontium and magnesium.

U.S. Pat. No. 4,104,478 discloses the hydrogenation of fatty acids in the presence of activated rhenium metal in combination with an extrinsic metal catalyst in the form of one of the platinum metals.

U.S. Pat. No. 4,113,662 discloses the hydrogenation of esters to alcohols in the presence of a catalyst comprising cobalt, zinc and copper at a pressure of 500–10,000 psig, preferably in the liquid phase.

We have found that the hydrogenation of carboxylic acids may be conducted in the vapor phase at moderate temperatures and pressures to provide good yields of the corresponding alcohols in the presence of an excess of water vapor over promoted ruthenium catalysts. We have further found that contacting the carboxylic acids in the presence of these catalysts at reaction temperature and pressures in the absence of an excess of water vapor results in the production of an ester of the carboxylic acid, wherein both the carboxylic acid and the ester functionality correspond to the reactant carboxylic acids.

SUMMARY OF THE INVENTION

It is therefore an object of the present invention to prepare alcohols from carboxylic acids in the vapor phase at moderate conditions of temperature and pressure.

It is a further object of the present invention to provide a process for the preparation of carboxylic acid esters in which both the acyl group and alkoxy group are derived from the reactant carboxylic acid in the vapor phase at moderate conditions of temperature and pressure.

In general, the process of the present invention includes the production of an alcohol by contacting a carboxylic acid with hydrogen in the vapor phase at a reaction temperature of from about 150° C. to about 450° C. and a reaction pressure of about 250 psig to 5,000 psig in the presence of an excess of water vapor and a catalyst comprising the mixed oxides of ruthenium, at least one of cobalt and nickel, optionally at least one of zinc and cadmium, and further optionally at least one of iron, copper, rhodium, palladium, osmium, iridium, and platinum.

An alternate embodiment of the invention includes the production of a carboxylic acid ester in which both the acyl group and alkoxy group are derived from the reactant carboxylic acid by contacting a carboxylic acid with hydrogen in the vapor phase at a reaction temperature of from about 150° C. to about 450° C. and a reaction pressure of about 250 psig to 5,000 psig in the absence of an excess of water vapor and in the presence of a catalyst comprising the mixed oxides of ruthenium, at least one of cobalt and nickel, optionally at least one of zinc and cadmium, and further optionally at least one of iron, copper, rhodium, palladium, osmium, iridium, and platinum.

DETAILED DESCRIPTION OF THE INVENTION

Carboxylic acids which are hydrogenated according to the present invention include aliphatic carboxylic acids having from one to about 10 carbon atoms. The process of the present invention is particularly suited to the hydrogenation of saturated carboxylic acids of the formula

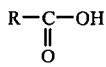

wherein R is a $C_{1-9}$ alkyl

Preferred carboxylic acids to be converted to their corresponding alcohols include acetic, n-butyric, isobutyric, propionic, valeric acids and the like. We expect that the process of the present invention and the catalysts utilized therein are suitable for the hydrogenation of higher carboxylic acids.

Catalysts suitable for use according to the process of the present invention include promoted ruthenium catalysts, preferably comprising the mixed oxides of ruthenium and promoter elements as set forth in the following empirical formula:

$$A_aRu_bD_cE_dO_x$$

wherein
A = Zn, Cd and mixtures thereof;
D = Co, Ni and mixtures thereof;
E = Fe, Cu, Rh, Pd, Os, Ir, Pt and mixtures thereof, and wherein
a = 0 to 1.0, preferably 0.01 to 1;
b = 0.01 to 3.0, preferably 0.1 to 1;
c = 0.01 to 3.0, preferably 0.1 to 2;

d=0 to 1.0, preferably 0.1 to 1; and, x=the number of oxygens determined by the valence requirements of the other elements present.

Preferably, A=Zn, D=Ni and Co, and E=Pd. It is additionally preferred that the sum of the numbers represented by a+d is greater than 0 and most preferably, that at least 3 of the preferred promoters named above are present together with the ruthenium. These catalysts may be prepared by methods known in the art, and may be supported or unsupported.

For example, these catalysts can be produced by evaporating a solution of soluble compounds containing the catalyst components, impregnating the solution followed by drying on an inert carrier, or mixing an aqueous slurry of insoluble compounds or free metals containing the catalytic components, optionally with an inert carrier, filtering, pressing, drying and calcining the filter cake, and finally grinding the filter cake to the desired particle size. The inert carriers which may be used with this catalyst include aluminates, silicates, titanates, zirconia, mixtures thereof, and the like. Soluble compounds include organic or inorganic salts of the metal compounds such as nitrates, halides, acetates, formates, phosphates and the like.

The catalyst used in the present invention is preferably at least partially reduced before utilization in the hydrogenation reaction. A suitable reductant is hydrogen gas. This pre-reduction may be carried out by contacting the catalyst with the reductant at a temperature of about 40° C. to about 300° C., preferably at a temperature of about 200° C. to about 300° C.

The hydrogenation reaction is conducted in the vapor phase at a temperature of about 150° C. to about 450° C., preferably between about 175° C. and 300° C. Reaction pressure is generally maintained between about 250 psig and about 5,000 psig, preferably 500 psig to 2500 psig. Hydrogen gas is introduced into the reaction, preferably in excess with respect to the carboxylic acid in a ratio of at least 2:1, preferably about 5:1 to about 100:1.

The carboxylic acid is preferably introduced into the reaction with a carrier such as water vapor, tetrahydrofuran, dioxane and esters of the carboxylic acid. The molar ratio of carrier (when present) to carboxylic acids is generally about 1:10 to about 100:1.

To obtain hydrogenation of the carboxylic acid, in contrast to the combined hydrogenation/esterification possible with the process of the present invention, an excess of water vapor should be introduced with the carboxylic acid into the reaction. By an excess of water is meant an amount greater than the amount of water vapor which is formed in situ by the nature of the hydrogenation reaction:

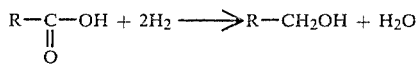

If no significant excess of water vapor is introduced in the reaction, the corresponding carboxylic acid ester of the carboxylic acid is formed, such as butyl butyrate from n-butyric acid.

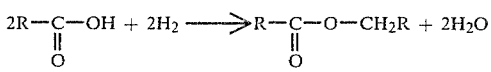

Inert diluent gases may also be introduced into the reactions, such as nitrogen, argon and the like.

SPECIFIC EMBODIMENTS OF THE INVENTION

In order to more clearly illustrate the present invention, the following working examples are presented. In these examples, the following definitions are used.

$$\% \text{ Conversion} = \frac{\text{Carboxylic acid reacted} \times 100}{\text{Carboxylic acid fed}}$$

$$\% \text{ Selectivity} = \frac{\text{Product produced} \times 100}{\text{Carboxylic acid reacted}}$$

$$\% \text{ Yield} = \frac{\text{Product produced} \times 100}{\text{Carboxylic acid fed}}$$

EXAMPLES 1-8

Catalysts of the formula $RuCoNiZn_{0.4}$ were prepared from the corresponding metal chlorides (hydrated) as set forth below. The hydrated chlorides of ruthenium, cobalt, and nickel were added in an amount sufficient to provide 0.015 moles of each metal, and zinc chloride in an amount sufficient to provide 0.06 moles of zinc was added to 250 ml of water with stirring for 30 minutes. Sodium hydroxide (50 wt.% aqueous) was added dropwise to the solution until the pH reached 8.3 (after the addition of approximately 10 ml). The resulting slurry was heated near boiling for 30 minutes with constant stirring, and then cooled. The pH was checked and adjusted, if necessary, to 7.5. The mixture was then filtered and washed with water, reslurried, filtered and washed again. The resulting solid mixed oxide was dried for about 16 hours at 125° C., calcined for about 3 hours at about 350° C., and was ground to pass 140 mesh (0.105 mm).

The mixed metal oxide catalysts were coated on Alundum alumina-silica supports (Norton Company) ground to 10 to 30 mesh (0.595 mm to 2.00 mm). 50 grams of the ground Alundum supports were placed in a jar. The supports were sprayed with a total of 5 grams distilled water in two additions with about 10 minutes rolling after each addition, to provide a partially wet surface. Mixed metal oxide, in an amount required to give 0.034 moles total "active" metal content, was added in two equal portions, with 15 minutes rolling after each addition. The coated catalyst was dried for about 16 hours at 125° C. and calcined 3 hours at 350° C. The resulting catalysts prepared in this manner contained approximately 5% by weight active metal component.

The catalysts prepared in the examples set forth herein were tested by charging approximately 40 cc of the subject catalysts to a 40 cc tubular stainless steel reactor. A furnace heated the reactor and hydrogen was charged to the reactor system to obtain the desired pressure. Before a reaction run, the system was at least partially pre-reduced for about 2 hours by passing hydrogen over the catalyst bed at 325 cc/min. at the desired run temperature. Prior to the 2 hour pre-reduction, the temperature of the catalyst bed was increased in 20° C. steps at 30 minutes intervals until the desired reaction temperature was reached. (In commercial practice, prereduction if any can be maintained from about 1 to about 24 hours or longer; if desired, so long as the catalyst is not entirely reduced to the metal species.)

At the start of the reaction run, the hydrogen feed rate was adjusted to the desired value. The carboxylic acid containing feed was introduced at an appropriate rate. For Examples 1-8, n-butyric acid was introduced as a vaporized solution of 10% acid in water (by weight). The reactor effluent was passed to ice bath-cooled glass condensers, and the liquid products were collected. The products were warmed to room temperature, weighed and analyzed by gas chromatography. The off-gases from the reactor also were routed to a gas chromatograph for analysis. The reaction conditions and test results for Examples 1-8 are reported in Table I.

EXAMPLES 9-11

Catalysts of the formula $RuCoNiZn_{0.4}O_x$ were prepared according to the procedure set forth in Examples 1-8. In these examples, the two hour pre-reduction was maintained at 275° C. instead of run temperature. These catalysts were tested for the hydrogenation of n-butyric acid as set forth in Examples 1-8. The reaction conditions and test results are set forth in Table II.

EXAMPLES 12-16

In Examples 12-16, catalysts of the composition $RuCoPdZn_{0.4}O_x$ were prepared and pre-reduced by the procedure set forth in Examples 9-11, except that palladium chloride was substituted for nickel chloride. These catalysts were tested for the hydrogenation of n-butyric acid to form n-butanol by the procedure set forth in claims 1-6. Reaction conditions and test results are reported in Table II.

EXAMPLE 17

A catalyst of the formula $RuCoPdZn_{0.4}O_x$ was prepared and pre-reduced according to the method set forth in Examples 12-16. This catalyst was tested for the hydrogenation of acetic acid at a temperature of 200° C. and a pressure of 1,000 psig. The hydrogen flow rate was 150 cc/min. and the acetic acid was introduced as the vapor of a 10% acid in water solution. The acetic acid was hydrogenated to ethanol by this method.

EXAMPLE 18

A catalyst of the formula $RuCoNiCd_{0.4}O_x$ was prepared and pre-reduced according to the procedure set forth in Examples 9-11, except that cadmium chloride was substituted for zinc chloride. This catalyst was tested for the hydrogenation of acetic acid according to the procedure and reaction conditions set forth in Example 17. Again ethanol was produced in good yields.

COMPARATIVE EXAMPLES 19-27

Catalysts represented by the formulas set forth in Table III were prepared according to the procedure of Examples 1-8. These catalysts were tested for the hydrogenation of n-butyric acid according to the procedure set forth in Examples 1-8. The tests were run at a reaction temperature of 220° C., a reaction pressure of 1000 psig, a hydrogen feed rate of 125 cc per minute, and a butyric acid feed rate of 20 cc per hour of the vapor from a solution of 9-10 wt.% butyric acid in water. Test results are reported in Table III.

EXAMPLES 28-31

Catalysts of the present invention represented by the formulas set forth in Table III were prepared and tested according to the procedure of Examples 1-8 and tested for the hydrogenation of n-butyric acid to n-butanol using the reaction conditions set forth in Comparative Examples 19-27. The test results reported in Table III demonstrate the superior results obtained when using the catalysts of the present invention for the hydrogenation of carboxylic acids. Reaction results using the catalyst of Example 4, which was run under the reaction conditions of the comparative examples, is also reported in Table III as Example 31 to provide further comparison.

EXAMPLES 32-34

Catalysts represented by the formula $RuCuNiZn_{0.4}O_x$ were prepared according to the procedure of Examples 1-8. These catalysts were tested for the production of n-butyl butyrate from n-butyric acid. N-butyric acid (100%) was fed in the vapor phase to the reaction at a rate of 20 cc (liquid) per hour. The reaction conditions and test results are reported in Table IV. The process of the present invention, utilizing promoted ruthenium mixed oxide catalysts, is selective for the production of the corresponding carboxylic acid esters of carboxylic acid, when the carboxylic acids are introduced to the reaction absent an excess of water vapor.

Thus it should be apparent to those skilled in the art that the subject invention accomplishes the objects set forth above. It is to be understood that the subject invention is not to be limited by the examples set forth herein. These have been provided merely to demonstrate operability, and the selection of ruthenium and promoter element containing compounds, methods of catalyst preparation, carboxylic acid feedstocks and reaction conditions can be determined from the total specification disclosure provided, without departing from the spirit of the invention herein disclosed and described, the scope of the invention including modifications and variations that fall within the scope of the attached claims.

TABLE I

Hydrogenation of N—Butyric Acid Over $RuCoNiZn_{0.4}O_x$ Catalysts

| Example No. | Temperature (°C.) | Pressure (PSIG) | H₂ Feed Rate (cc/Min.) | % Conversion | n-Butanol % Yield | % Selectivity |
|---|---|---|---|---|---|---|
| 1 | 210 | 1250 | 150 | 71.6 | 69.1 | 96.5 |
| 2 | 220 | 1300 | 150 | 91.9 | 65.0 | 70.7 |
| 3 | 220 | 1300 | 150 | 99.0 | 71.7 | 72.9 |
| 4* | 220 | 1000 | 325 | 62.8 | 53.9 | 85.8 |
| 5 | 220 | 1000 | 325 | 55.8 | 53.2 | 95.3 |
| 6 | 250 | 1200 | 325 | 55.4 | 40.2 | 72.6 |
| 7 | 250 | 1200 | 325 | 52.6 | 49.1 | 93.3 |
| 8 | 220 | 1000 | 650 | 56.4 | 21.9 | 38.8 |

Butyric Acid Feed Rate = 10 cc (Liquid)/Hr.
Butyric Acid Feed 10% Acid By Weight Aqueous
*Butyric Acid Feed Rate = 20 cc (Liquid)/Hr.

TABLE II

Hydrogenation of N—Butyric Acid Over $RuCoMZn_{0.4}O_x$ Catalysts

| Example No. | M-Metal Component | Temperature (°C.) | Pressure (PSIG) | % Conversion | N—Butanol % Yield | % Selectivity |
|---|---|---|---|---|---|---|
| 9 | Ni | 200° | 1000 | 37 | 33 | 89 |
| 10 | Ni | 205° C. | 1200 | 52 | 50 | 96 |
| 11 | Ni | 215° | 1250 | 83 | 39 | 47 |
| 12 | Pd | 210° | 1250 | 98 | 69 | 71 |
| 13 | Pd | 200° | 1000 | 84 | 73 | 87 |
| 14 | Pd | 200° | 1000 | 74 | 71 | 97 |

TABLE II-continued

Hydrogenation of N—Butyric Acid Over $RuCoMZn_{0.4}O_x$ Catalysts

| Example No. | M-Metal Component | Temperature (°C.) | Pressure (PSIG) | % Conversion | N—Butanol % Yield | % Selectivity |
|---|---|---|---|---|---|---|
| 15 | Pd | 200° | 1000 | 75 | 73 | 97 |
| 16 | Pd | 200° | 1100 | 77 | 76 | 98 |

$H_2$ Feed Rate = 150 cc/min
Butyric Acid Feed Rate = 10 cc (Liquid)/Hr.
Butyric Acid Fed 10% Acid By Weight (Aqueous)

TABLE III

Hydrogenation of N—Butyric Acid Over Various Catalysts

| Example No. | Catalyst | % Yield N—Butanol | % Yield $CH_4$ |
|---|---|---|---|
| C 19 | $RuO_x$ | — | 28.8 |
| C 20 | $NiO_x$ | trace | 0.9 |
| C 21 | $CoO_x$ | 5.5 | — |
| C 22 | $CoNiO_x$ | trace | — |
| C 23 | $RuZn_{0.5}O_x$ | 3.5 | 23.1 |
| C 24 | $NiZnO_{0.5}O_x$ | trace | — |
| C 25 | $CoZn_{0.5}O_x$ | 11.5 | — |
| C 26 | $CoNiZn_{0.5}O_x$ | trace | — |
| C 27 | $CoNiZn_{0.5}O_x$ | 1.7 | — |
| 28 | $RuNiCoO_x$ | 43.5 | — |
| 29 | $RuNiZn_{0.5}O_x$ | 36.9 | 0.7 |
| 30 | $RuCoZn_{0.5}O_x$ | 23.2 | 11.6 |
| 31 | $RuCoNiZn_{0.4}O_x$ | 53.9 | 2.3 |

TABLE IV

Preparation of N—Butyl-Butyrate Over $RuCoNiZn_{0.4}O_x$ Catalysts

| Example No. | Temperature °C. | Pressure (PSIG) | $H_2$ Feed Rate (cc/Min.) | % Conversion | % Selectivity To N—Butyl Butyrate* | % Selectivity To N—Butanol |
|---|---|---|---|---|---|---|
| 32 | 220 | 1000 | 325 | 53.9 | 45 | trace |
| 33 | 240 | 1000 | 650 | 57.9 | 35 | trace |
| 34 | 270 | 1200 | 650 | 52.0 | 80 | 11.3 |

*Estimated Based Upon conversion and absence of other products - includes butyric acid incorporated into ester product
N—Butyric Acid (100%) Feed Rate = 20 cc (Liquid)/Hour

We claim:

1. A process for the production of carboxylic acid esters having from 2 to 20 carbon atoms from aliphatic carboxylic acids having from 1 to 10 carbon atoms, including contacting said carboxylic acids with hydrogen in the vapor phase in the absence of water in excess of the amount of water vapor formed in situ, at a reaction temperature from about 150° C. to about 450° C. and a reaction pressure of about 250 psig to about 5000 psig in the presence of a catalyst represented by the formula $$Zn_aRu_bD_cE_dO_x$$

wherein
D = Co, Ni and mixtures thereof;
E = Cd, Fe, Cu,, Rh, Pd, Os, Ir, Pt and mixtures thereof;
and wherein
a = greater than 0 to 1,
b = 0.01 to 3,
c = 0.01 to 3,
d = 0 to 1,
x = the number of oxygens determined by the valence requirements of the other elements.

2. A process as set forth in claim 1 wherein butyl butyrate is produced from butyric acid.

3. A process as set forth in claim 1 wherein said catalyst contains Co.

4. A process as set forth in claim 1 wherein said catalyst contains Ni.

5. A process as set forth in claim 1 wherein said catalyst contains Co and Ni.

6. A process as set forth in claim 1 wherein said catalyst is represented by the formula $RuCoNiZn_{0.4}O_x$.

* * * * *